United States Patent [19]

Houlihan et al.

[11] 3,978,132

[45] Aug. 31, 1976

[54] ACYL BENZYL ETHERS

[75] Inventors: William J. Houlihan, Mountain Lakes; Jeffrey Nadelson, Lake Parsippany, both of N.J.

[73] Assignee: Sandoz, Inc., E. Hanover, N.J.

[22] Filed: Feb. 12, 1975

[21] Appl. No.: 549,358

Related U.S. Application Data

[63] Continuation-in-part of Ser. No. 422,540, Dec. 6, 1973, abandoned.

[52] U.S. Cl............................. 260/590 D; 424/331
[51] Int. Cl.²......................................... C07C 49/84
[58] Field of Search...................... 260/590 D, 592

[56] References Cited
UNITED STATES PATENTS

| | | | |
|---|---|---|---|
| 2,109,458 | 3/1938 | Bass et al. | 269/592 |
| 3,697,581 | 10/1972 | Humber | 260/612 R |
| 3,813,419 | 5/1974 | Bach et al. | 260/612 R |
| 3,884,961 | 5/1975 | Houlihan et al. | 260/592 |

OTHER PUBLICATIONS

Kornblum et al., J.A.C.S., vol. 85, pp. 1141–1147, (1963).

Primary Examiner—James O. Thomas, Jr.
Assistant Examiner—James H. Reamer
Attorney, Agent, or Firm—Gerald D. Sharkin; Robert S. Honor

[57] ABSTRACT

Acyl substituted or unsubstituted benzyl ethers, e.g., p-(phenoxymethyl)pivalophenone, are prepared by reacting a corresponding α-bromo-p-pivaloyl toluene with a corresponding phenol and are useful as hypolipidemic agents.

7 Claims, No Drawings

ACYL BENZYL ETHERS

This application is a continuation-in-part of copending application Ser. No. 422,540, now abandoned filed Dec. 6, 1973.

This invention relates to acyl benzyl ethers which exhibit hypolipidemic activity. In particular, it relates to acyl substituted or unsubstituted benzyl ethers and to their preparation.

The compounds of this invention may be represented by the following structural formula:

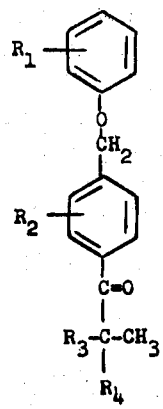

(I)

where $R_1$ and $R_2$ each independently represent hydrogen, halo having an atomic weight of about 19 to 36, or straight chain lower alkyl, i.e., straight chain alkyl having 1 to 4 carbon atoms, e.g., methyl, ethyl, propyl and the like, and $R_3$ and $R_4$ each independently represent lower alkyl having 1 to 2 carbon atoms, i.e., methyl or ethyl.

The compounds of formula (I) are prepared according to the following reaction scheme:

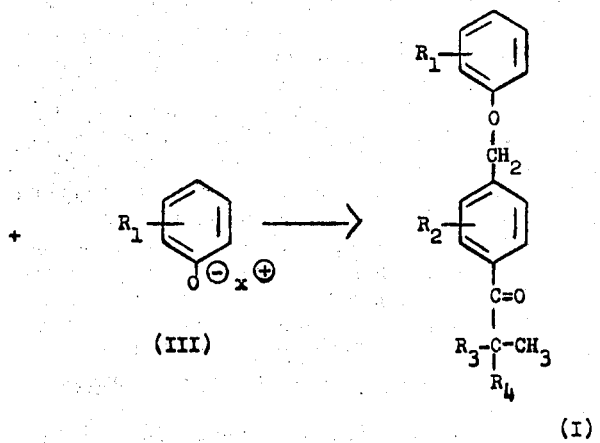

where

X is sodium, potassium or lithium, and
$R_1$, $R_2$, $R_3$ and $R_4$ are as defined above.

The compounds of formula (I) are prepared by treating a compound of the formula (II) with a compound of the formula (III) in the presence of an organic solvent. The compounds of formula (III) are generated by treatment of a corresponding phenol with an inorganic base such as an alkali metal hydroxide such as sodium hydroxide, potassium hydroxide and the like, an alkali metal alkoxide such as sodium methoxide, sodium ethoxide, potassium methoxide and the like, or an alkali metal hydride such as sodium hydride, the latter being especially preferred. The particular solvent used is not critical, but it is preferred that the reaction be carried out in the presence of the lower alkanols, e.g., methanol, ethanol and the like, the aromatic hydrocarbons, such as benzene, toluene and the like, dimethylformamide, or dimethylacetamide, the latter being especially preferred. The temperature of the reaction is not critical, but it is preferred that the reaction be carried out at a temperature between about 0° to 60°C., preferably from about 20° to 30°C. The reaction may be run from about 2 to 36 hours, preferably 15 to 20 hours. The product is recovered using conventional techniques, e.g., evaporation followed by trituration.

The compounds of formula (II) are prepared according to the following reaction scheme:

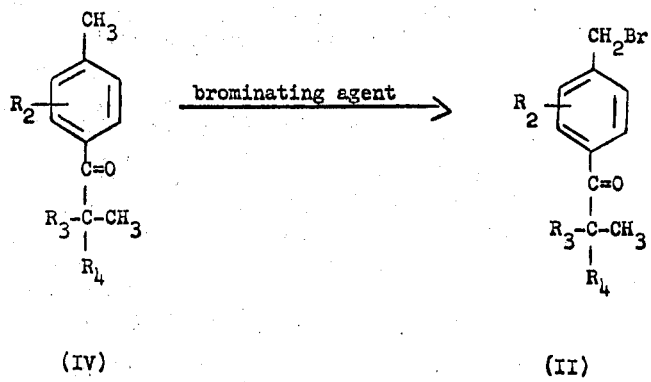

where $R_2$, $R_3$ and $R_4$ are as defined above.

The compounds of formula (II) are prepared by treating a compound of formula (IV) with a brominating agent in the presence of an inert organic solvent and free radical initiator. The brominating agent which can be used is bromine, N-bromosuccinamide, N-bromo phthalamide, N-bromoacetamide and the like. The particular agent used is not critical, but N-bromosuccinamide is preferred. In the preferred process, the free radical initiator used is an organic peroxide, especially benzoyl peroxide. The reaction can also be carried out under ultraviolet light. Although the particular solvent used is not critical, the preferred solvents are the halogenated hydrocarbons such as methylene dichloride, chloroform, carbon tetrachloride and the like, although the aromatic hydrocarbons such as benzene can also be employed. The temperature of the reaction is not critical, but reflux temperature of the solvent is preferred. The reaction is run for about 12 to 48 hours; preferably 18 to 25 hours. The product is recovered by conventional techniques, e.g., crystallization.

Many of the compounds of formulae (III) and (IV) are known and may be prepared by methods described in the literature. The compounds of formulae (III) and (IV) not specifically disclosed may be prepared by analogous methods from known starting materials.

The compounds of formula (I) are useful because they possess pharmacological activity in animals as hypolipidemic agents, particularly as hypolipoproteinemic agents as indicated by the fall in cholesterol and triglyceride levels in male albino Wistar rats weighing 110 to 130 g. initially. The rats are maintained on drug-free laboratory chow diet for seven days and then divided into groups of 8 to 10 animals. Each group with the exception of the control is then given orally 30 to 250 milligrams per kilogram of body weight per diem of the compound for six days. At the end of this period, the animals are anesthetized with sodium hexobarbital and bled from the carotid arteries. Serum or plasma samples are collected, and 1.0 ml. samples of the serum are added to 9.0 ml. redistilled isopropanol. Two autoanalyzer cupsful of a mixture of zeolite-copper hydroxide and Lloydds reagent (Kessler, E., and Lederer, H., 1965, Technicon Symposium, Mediad, Inc., New York, 345–347) are added, and the mixture is shaken for one hour. Cholesterol and triglyceride levels are determined simultaneously on the same sample by Technicon N 24 A (cholesterol) and N 78 (triglyceride) methodology. The mean total serum cholesterol levels are then computed and the hypocholesterolemic activity is expressed as the fall in cholesterol levels as a percentage of the control level. The change in serum triglyceride levels induced by the drug is computed as a percentage of the control triglyceride levels.

For such usage, the compounds (I) may be combined with a pharmaceutically acceptable carrier or adjuvant and may be administered orally or parenterally as such or admixed with conventional pharmaceutical carriers. They may be administered in such forms as tablets, dispersible powders, granules, capsules, syrups and elixirs and parenterally as solutions, suspensions, dispersions, emulsions and the like, e.g., a sterile injectable aqueous solution. The dosage will vary depending upon the mode of administration utilized and the particular compound employed.

The hypolipidemic effective dosage of compounds (I) employed in the alleviation of lipidemia may vary depending on the particular compound employed and the severity of the condition being treated. However, in general, satisfactory results are obtained when the compounds of formula (I) are administered at a daily dosage of from about 4.0 milligrams to about 250 milligrams per kilogram of animal body weight, preferably given in divided doses two to four times a day, or in sustained release form. For most large mammals, the total daily dosage is from about 250 milligrams to about 3000 milligrams. Dosage forms suitable for internal use comprise from about 62.5 to about 1500 milligrams of the active compound in intimate admixture with a solid or liquid pharmaceutically acceptable carrier or diluent.

A representative formulation suitable for oral administration two to four times a day for the treatment of lipidemia is a capsule prepared by standard encapsulating techniques which contains the following:

| Ingredient | Weight (mg.) |
|---|---|
| p-(phenoxymethyl)pivalophenone | 150 |
| inert solid diluent (starch, lactose, kaolin) | 300 |

EXAMPLE 1

α-bromo-p-pivaloyl toluene

To a suspension of 28.5 g. (1.17 g. atoms) magnesium turnings in 150 ml. tetrahydrofuran under a nitrogen atmosphere there is added 10 ml. of 4-bromotoluene (1.17 mole) in 650 ml. dry tetrahydrofuran, the reaction is started and the remainder of the bromotoluene solution is added dropwise at a rate that maintains a moderate reflux. After the addition is complete, the mixture is refluxed for an additional 1 ½ hours. The resulting Grignard solution is added dropwise to a cold solution of 128.0 g. pivaloyl chloride (1.06 mole) in 500 ml. dry tetrahydrofuran at a rate that maintains the temperature at 0° to −5°C. The solution is stirred for an additional 1 ½ hours at 0° and then at room temperature for 18 hours. The mixture is then cooled to 0° and hydrolyzed by the addition of 100 ml. 2N hydrochloric acid. The layers are separated and 200 ml. of ether is added to the organic phases which is then washed respectively with 100 ml. 2N hydrochloric acid, 100 ml. 10% sodium bicarbonate solution and 100 ml. saturated sodium chloride. The resulting layer is dried over anhydrous sodium sulfate, filtered, and the solvent is removed in vacuo to give p-pivaloyl toluene (b.p. 80°–84°C./0.7 mm, $n_D^{21}$ 1.5108). A mixture of 156.3 g. (0.886 mole) of the resulting p-pivaloyl toluene is then added to 157.8 g. (0.886 mole) N-bromosuccinamide, 4.0 g. (0.016 mole) benzoyl peroxide and 150 ml. carbon tetrachloride and heated at reflux for 18 hours. The mixture is cooled and filtered and the resulting precipitate is washed with carbon tetrachloride. The solvents are removed in vacuo and the resulting oil is distilled in vacuo to give α-bromo-p-pivaloyl toluene (b.p. 124°–132°C./0.7 mm, $n_D^{22}$ 1.5546-V.P.C. 96% monobromo 4%-dibromo).

Following the above procedure and using in place of 4-bromotoluene equivalent amounts of:
  a. 4-bromo-2-chlorotoluene, or
  b. 4-bromo-3-methyltoluene,
there is obtained
  a. α-bromo-2-chloro-4-pivaloyl toluene, or
  b. α-bromo-3-methyl-4-pivaloyl toluene, respectively.

EXAMPLE 2 p-(phenoxymethyl)-pivalophenone

To a suspension of 6.73 g. sodium hydride (57% suspension in mineral oil-0.165 mole) in 200 ml. dry dimethylacetamide, there is added dropwise 14.1 g. (0.15 mole) of phenol in 50 ml. dimethylacetamide maintaining the temperature below 25°C. After the addition is complete, the resulting mixture is stirred for 1 ½ hours at room temperature. A solution of 38.3 g. (0.15 mole) α-bromo-p-pivaloyl toluene in 50 ml. dimethylacetamide is then added dropwise at room temperature and the resulting mixture is stirred for 18 hours at room temperature. The mixture is then treated with 10 ml. of methanol and the solvent removed in vacuo. The resulting residue is partitioned between ether and water, and the ether layer is washed twice with 200 ml. of 2N sodium hydroxide, once with water and once with brine. The organic layers are combined and dried over anhydrous magnesium sulfate, decolorized and evaporated. The resulting solid is triturated with petroleum ether to give p-(phenoxymethyl)-pivalophenone, m.p. 79.5° to 80°C.

Following the above procedure and using in place of α-bromo-p-pivaloyl toluene an equivalent amount of:
a. α-bromo-2-chloro-4-pivaloyl toluene, or
b. α-bromo-3-methyl-4-pivaloyl toluene,
there is obtained
a. p-(phenoxymethyl)-2-chloro-pivalophenone, or
b. p-(phenoxymethyl)-3-methyl-pivalophenone, respectively.

Again following the above procedure and using in place of phenol an equivalent amount of
a. 4-chlorophenol,
b. 3-chlorophenol, or
c. 4-methylphenol,
there is obtained
a. p-(4-chlorophenoxymethyl)pivalophenone,
b. p-(3-chlorophenoxymethyl)pivalophenone, or
c. p-(4-methylphenoxymethyl)pivalophenone, respectively.

The p-(phenoxymethyl)pivalophenone of this example is an effective hypolipidemic agent when orally administered to an animal suffering from lipidemia at a dosage of 150 mg. four times a day.

What is claimed is:

1. A compound of the formula

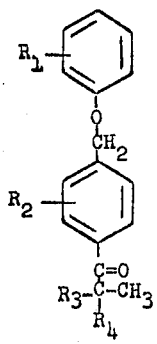

where
$R_1$ and $R_2$ each independently represent hydrogen, halo having an atomic weight of about 19 to 36, or straight chain lower alkyl having 1 to 4 carbon atoms, and
$R_3$ and $R_4$ each independently represent lower alkyl having 1 to 2 carbon atoms.

2. A compound of the formula

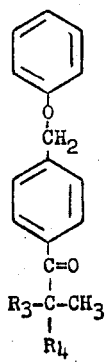

where $R_3$ and $R_4$ are as defined in claim 1.

3. A compound of the formula

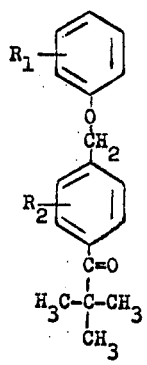

where $R_1$ and $R_2$ are as defined in claim 1.

4. The compound of claim 1 which is p-(phenoxymethyl)-pivalophenone.

5. The compound of claim 1 which is p-(4-chlorophenoxymethyl)pivalophenone.

6. The compound of claim 1 which is p-(3-chlorophenoxymethyl)pivalophenone.

7. The compound of claim 1 which is p-(4-methylphenoxymethyl)pivalophenone.

* * * * *